United States Patent
Yamauchi

(10) Patent No.: US 10,743,015 B2
(45) Date of Patent: Aug. 11, 2020

(54) ENDOSCOPE APPARATUS AND IMAGING METHOD

(71) Applicant: OLYMPUS CORPORATION, Tokyo (JP)

(72) Inventor: Hideyoshi Yamauchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/977,315

(22) Filed: May 11, 2018

(65) Prior Publication Data
US 2018/0338152 A1    Nov. 22, 2018

(30) Foreign Application Priority Data

May 17, 2017    (JP) .................. 2017-098347

(51) Int. Cl.
| | |
|---|---|
| *H04N 19/46* | (2014.01) |
| *H04N 7/01* | (2006.01) |
| *A61B 1/00* | (2006.01) |
| *A61B 1/045* | (2006.01) |
| *H04N 19/115* | (2014.01) |
| *H04N 5/232* | (2006.01) |
| *H04N 5/225* | (2006.01) |
| *A61B 1/005* | (2006.01) |

(52) U.S. Cl.
CPC ........ *H04N 19/46* (2014.11); *A61B 1/00009* (2013.01); *A61B 1/00018* (2013.01); *A61B 1/00059* (2013.01); *A61B 1/00096* (2013.01); *A61B 1/00101* (2013.01); *A61B 1/00174* (2013.01); *A61B 1/045* (2013.01); *H04N 5/2259* (2013.01); *H04N 5/23209* (2013.01); *H04N 7/0127* (2013.01); *H04N 19/115* (2014.11); *A61B 1/005* (2013.01); *H04N 5/2329* (2013.01); *H04N 2005/2255* (2013.01)

(58) Field of Classification Search
CPC .... H04N 19/46; H04N 19/115; H04N 5/2329; H04N 7/0127; A61B 1/00009; A61B 1/00018; A61B 1/00059; A61B 1/00096; A61B 1/00101; A61B 1/00174; A61B 1/045
USPC ............................................. 348/71
See application file for complete search history.

(56) References Cited

U.S. PATENT DOCUMENTS

| | | | | |
|---|---|---|---|---|
| 2010/0315496 | A1* | 12/2010 | Miyayashiki | .......... H04N 7/183 348/65 |
| 2013/0012777 | A1* | 1/2013 | Baum | ................ A61B 1/00013 600/110 |
| 2015/0138328 | A1* | 5/2015 | Yokohama | ......... A61B 1/00018 348/65 |

FOREIGN PATENT DOCUMENTS

JP    2012014129 A    1/2012

* cited by examiner

*Primary Examiner* — Nguyen T Truong
(74) *Attorney, Agent, or Firm* — Scully, Scott, Murphy & Presser, P.C.

(57) ABSTRACT

An endoscope apparatus includes: an imager having a photoelectric converter that performs a photoelectric conversion of an optical signal into a video signal, and a compressor that compresses the video signal; and a controller that changes a compression ratio in a compression of the video signal in accordance with a preset condition.

10 Claims, 5 Drawing Sheets

FIG. 5

| LENGTH OF INSERTION SECTION | TRANSMISSION CAPABLE TRANSMISSION RATE | FLAME RATE COMPRESSION RATIO | FLAME RATE COMPRESSION RATIO |
|---|---|---|---|
| 2.0m | 2.4Gbps | 120fps 1/2 | 240fps 1/4 |
| 3.5m | 2.4Gbps | 120fps 1/2 | 240fps 1/4 |
| 5.0m | 2.4Gbps | 120fps 1/2 | 240fps 1/4 |
| 7.5m | 2.4Gbps | 120fps 1/2 | 240fps 1/4 |
| 10.0m | 2.4Gbps | 120fps 1/2 | 240fps 1/4 |
| 12.0m | 1.2Gbps | 120fps 1/4 | 240fps 1/8 |
| 18.0m | 0.6Gbps | 120fps 1/8 | 240fps 1/16 |
| 20.0m | 0.6Gbps | 120fps 1/8 | 240fps 1/16 |
| 30.0m | 0.3Gbps | 120fps 1/16 | 240fps 1/32 |

ENDOSCOPE APPARATUS AND IMAGING METHOD

BACKGROUND

Technical Field

The present invention relates to an endoscope apparatus and an imaging method. Priority is claimed on Japanese Patent Application No. 2017-098347, filed May 17, 2017, the content of which is incorporated herein by reference.

Background Art

Conventionally, an endoscope apparatus is generally configured to include an endoscope for obtaining an observation image by inserting an insertion section into an observation target, and a display section for displaying the observation image.

By using this type of endoscope apparatus, at the same time that the insertion section of the endoscope is inserted into the observation part, the inspection can be performed while observing the observation image displayed on the display section such as a monitor, that is, the endoscopic image. Therefore, it is possible for the inspector to perform the inspection without any discomfort and also to display the desired observation image reliably on the monitor or the like for recognition.

Further, in actual inspection, there is a case in which the inspector performs only simple inspection at the inspection site, records the captured endoscopic image on a moving image file or the like, and thereafter reproduces the moving image file to perform detailed inspection. In such a case, it is required to effectively use the capacity of the recording medium for recording the moving image file and the like.

Therefore, an endoscope apparatus has been proposed in which the amount of movement of the insertion section of the endoscope is detected, and the imaging condition is changed according to the amount of movement. For example, Japanese Unexamined Patent Application, First Publication No. 2012-14129 discloses an endoscope apparatus capable of efficiently using the capacity of the recording medium by reducing the amount of data to be recorded on the recording medium according to the moving speed of the distal end of the insertion section.

In this endoscope apparatus, an acceleration sensor is provided at the distal end of the insertion section, and the moving speed of the insertion section is calculated based on the value output from the acceleration sensor. When the moving speed of the insertion section is fast, the frame rate of the moving image to be recorded is raised, thereby preventing image from being missed. When the moving speed of the insertion section is slow, the frame rate of the moving image to be recorded is lowered, thereby saving the capacity of the recording medium.

SUMMARY

The present invention provides an endoscope apparatus capable of long-length transmission of image data without reducing the number of pixels and at the same time reducing the influence of rolling shutter distortion by increasing the frame rate. Also, the present invention provides an endoscope apparatus capable of operating at a frame rate and a compression ratio so as to achieve an optimum transmission rate according to the type/mode of the optical adapter and the type of the insertion section.

An aspect of the present invention is an endoscope apparatus including: an imager having a photoelectric converter that performs a photoelectric conversion of an optical signal into a video signal, and a compressor that compresses the video signal; and a controller configured to change a compression ratio in a compression of the video signal in accordance with a preset condition.

An aspect of the present invention is an imaging method using an endoscope apparatus including an imager having a photoelectric converter that performs a photoelectric conversion of an optical signal into a video signal and a compressor that compresses the video signal, wherein the imaging method includes: a step of determining a type of an insertion section; and a step of changing at least one of a compression ratio of the compressor and a frame rate of the photoelectric conversion in accordance with the type of the insertion section.

An aspect of the present invention is an imaging method using an endoscope apparatus including an imager having a photoelectric converter that performs a photoelectric conversion of an optical signal into a video signal and a compressor that compresses the video signal, wherein the imaging method includes: a step of determining a type of an optical adapter mounted on the imager; and a step of changing at least one of a compression ratio of the compressor and a frame rate of the photoelectric conversion in accordance with the type of the optical adapter.

BRIEF DESCRIPTION OF THE DRAWINGS

FIG. 5 is a table showing the correspondence between the length of the insertion section and the frame rate/compression ratio in the frame rate/compression ratio changing process based on the type of the optical adapter of the endoscope apparatus according to the second embodiment of the present invention.

DETAILED DESCRIPTION OF THE PREFERRED EMBODIMENTS

Hereinafter, an endoscope apparatus according to an embodiment of the present invention will be described, referring to figures.

Figure 1:
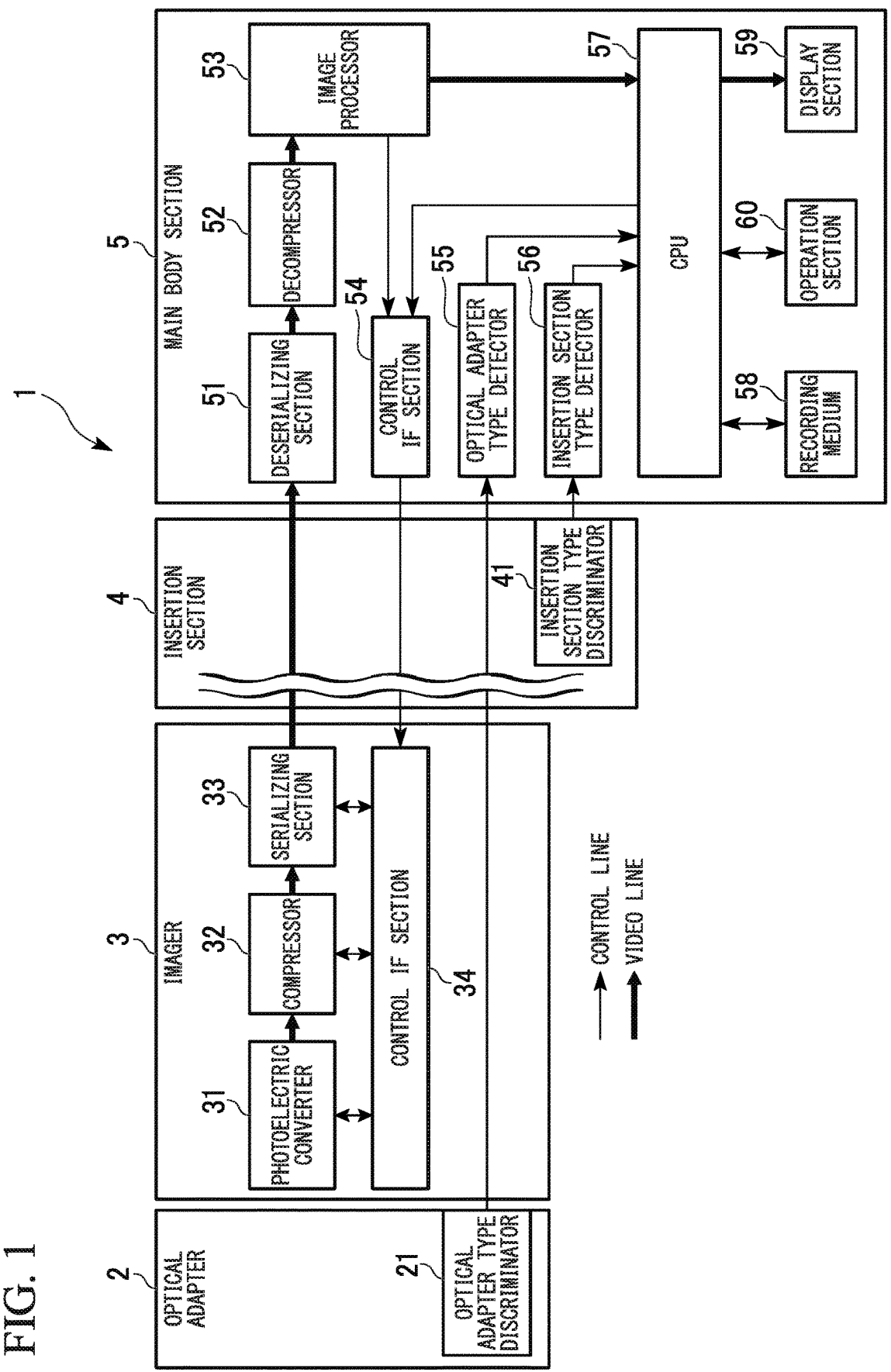
FIG. 1 is a block diagram showing the overall configuration of an endoscope apparatus according to an embodiment of the present invention.

FIG. 1 is a block diagram showing the overall configuration of an endoscope apparatus according to an embodiment of the present invention. The endoscope apparatus 1 includes an optical adapter 2, an imager 3, an insertion section 4, and a main body section 5. The insertion section 4 has an elongated tubular shape that can be bent from the distal end to the proximal end, and is inserted into the subject. The imager 3 is provided at the distal end of the insertion section 4. The optical adapter 2 is attached to the imager 3. A main body section 5 is provided at a proximal end of the insertion section 4.

The optical adapter 2 includes an optical adapter type discriminator 21. The optical adapter type discriminator 21 determines the type of the optical adapter 2, for example, by reading the value of the resistance embedded in the optical adapter 2. In the present embodiment, the optical adapter 2 is an optical adapter of optical path switching type (optical adapter for measurement or optical adapter for direct viewing/side viewing switching type), and is provided with an optical system forming a plurality of optical paths with parallax. By switching the plurality of optical paths in a sequence, it is possible for one imager 3 to form a plurality of parallactic subject images.

The imager 3 includes a photoelectric converter 31, a compressor 32, a serializing section 33, and a control IF section 34. The photoelectric converter 31 performs a photoelectric conversion of the subject image formed via the optical adapter 2 at a certain frame rate to generate a video signal (RAW image data). The video signal is input to the compressor 32 and compressed at a desired compression ratio. The compressed video signal is input to the serializing section 33. The serializing section 33 serializes the compressed video signal to convert it into serial data, and sequentially outputs serial data signals. The control IF section 34 controls the photoelectric converter 31, the compressor 32, and the serializing section 33.

The insertion section 4 includes an insertion section type discriminator 41. The insertion section type discriminator 41 determines the type of the insertion section 4, for example, by reading the value of the resistance embedded in the insertion section 4. The type of the insertion section 4 includes the length of the insertion section 4, the size of the diameter of the transmission path in the insertion section, and the like. The serial data signal is transmitted to the main body section 5 via the composite coaxial line provided in the insertion section 4.

The main unit 5 includes a deserializing section 51, a decompressor 52, an image processor 53, a control IF section 54, an optical adapter type detector 55, an insertion section type detector 56, a CPU 57 (controller), a recording medium 58, a display section 59, and an operation section 60.

The serial data signal transmitted from the imager 3 via the insertion section 4 is input to the deserializing section 51. The deserializing section 51 deserializes the transmitted serial data signal and decodes it into a parallel signal. The decompressor 52 decompresses the parallel signal and decodes the video signal output from the photoelectric converter 31. The image processor 53 performs image processing on the video signal and transmits image data to the CPU 57. The CPU 57 causes the display section 59 to display the image data (video), and causes the recording medium 58 to record a still image or a moving image based on a user operation on the operation section 60.

The control IF section 54 transmits control signals from the image processor 53 and the CPU 57 to the control IF section 34 of the imager 3 via the insertion section 4. The optical adapter type detector 55 receives the information (data) relating to the type of the optical adapter 2 read by the optical adapter type discriminator 21, and transmits the information to the CPU 57. As a result, the CPU 57 determines the type of the optical adapter 2. The insertion section type detector 56 receives the information (data) relating to the type of the insertion section 4 read by the insertion section type discriminator 41, and transmits the information to the CPU 57. As a result, the CPU 57 determines the type of the insertion section 4. In this way, the CPU 57 determines the type of the optical adapter 2 and the type of the insertion section 4.

Although high-speed transmission is performed in the imager 3, there is a limit to transmission speed based on the length and diameter of the insertion section 4. When the transmission speed exceeds the limit, it becomes impossible to display the video. Also, when the attached optical adapter is of a type that switches among a plurality of optical paths, unless a larger number of frames are transmitted than in the case of an optical adapter using a single optical path, images having the same degree of image quality as in the case of the optical adapter using a single optical path cannot be obtained.

Therefore, the CPU 57 determines the optimum frame rate/compression ratio in accordance with the type of the optical adapter 2 and the type of the insertion section 4, and the endoscope apparatus operates based on the determined optimum frame rate/compression ratio.

Figures 2, 3:
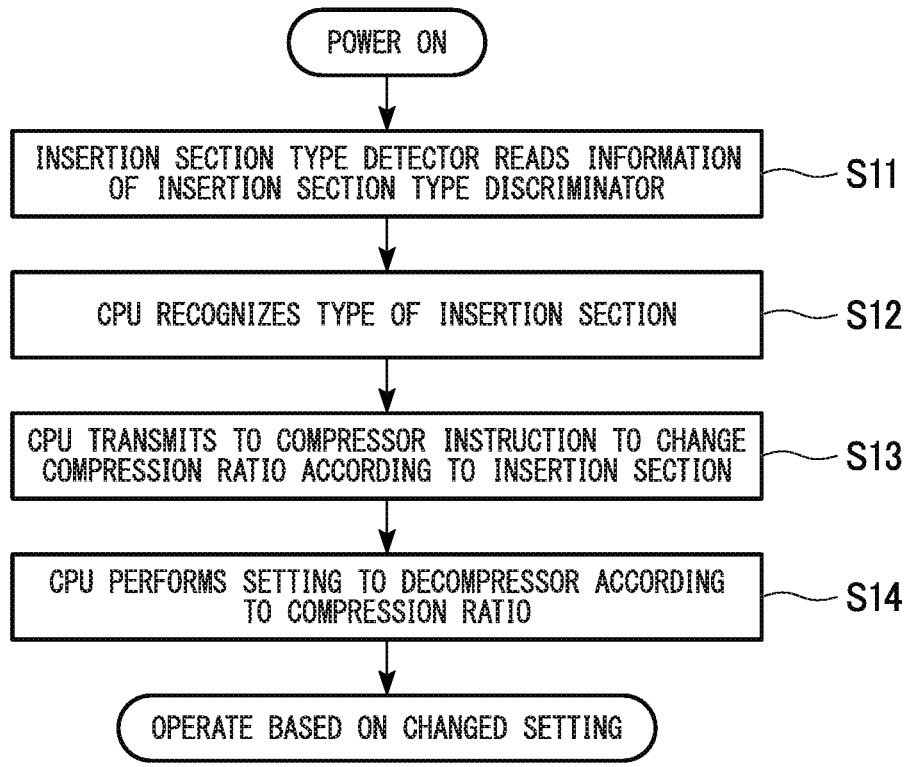
FIG. 2 is a flowchart showing a compression ratio changing process based on the type of an insertion section of an endoscope apparatus according to a first embodiment of the present invention.
FIG. 3 is a table showing the correspondence between the length of the insertion section and the compression ratio in the compression ratio changing process based on the type of the insertion section of the endoscope apparatus according to the first embodiment of the present invention.

Next, the compression ratio changing process based on the type of the insertion section of the endoscope apparatus according to the first embodiment of the present invention will be described. FIG. 2 is a flowchart showing a compression ratio changing process based on the type of the insertion section of the endoscope apparatus according to the present embodiment. In the present embodiment, the compression ratio in the compression of the video signal by the compressor 32 is changed in accordance with the type of the insertion section 4.

When the apparatus is activated, firstly, the insertion section type detector 56 of the main body section 5 reads the information (data) relating to the insertion section type discriminator 41 of the insertion section 4 (step S11) and transmits it to the CPU 57. The CPU 57 determines the type of the insertion section 4 based on the transmitted data (step S12). In the CPU 57, the type information on each type of the insertion section 4 is stored as a database. The type information of the insertion section 4 includes the length of the insertion section 4, the size of the diameter of the transmission path in the insertion section, and the like.

FIG. 3 is a table showing the correspondence between the length of the insertion section 4, transmission capable transmission rate, and the compression ratio in the compression ratio changing process based on the length of the insertion section of the endoscope apparatus 1 according to the present embodiment. In FIG. 3, the frame rate is fixed at 60 fps. As shown in the table of FIG. 3, the transmission capable transmission rate and the compression ratio are determined in advance for each length of the insertion section 4. Based on this table, the CPU 57 decides a compression ratio so as to achieve a transmission capable transmission rate, and transmits an instruction to change (set) the compression ratio to the compressor 32 via the control IF sections 54 and 34 (Step S13).

Further, the CPU 57 sets the decompression ratio of the decompressor 52 so as to correspond to the compression ratio set by the compressor 32 (step S14). As a result, the compressor 32 compresses the video signal at the set compression ratio, and the decompressor 52 decompresses with the decompression ratio corresponding to the set compression ratio.

By performing the compression ratio changing process in this manner, it is possible to perform long-length transmission of image data while maintaining the frame rate. Further, since the compression ratio is determined by automatically determining the type of the insertion section, complicated work is unnecessary. Since the optical adapter 2 does not contribute to changing the compression ratio, this embodiment can be applied to the case when the optical adapter 2 is absent. In that case, the optical adapter type detector 55 in the configuration of FIG. 1 is unnecessary.

Figure 4:
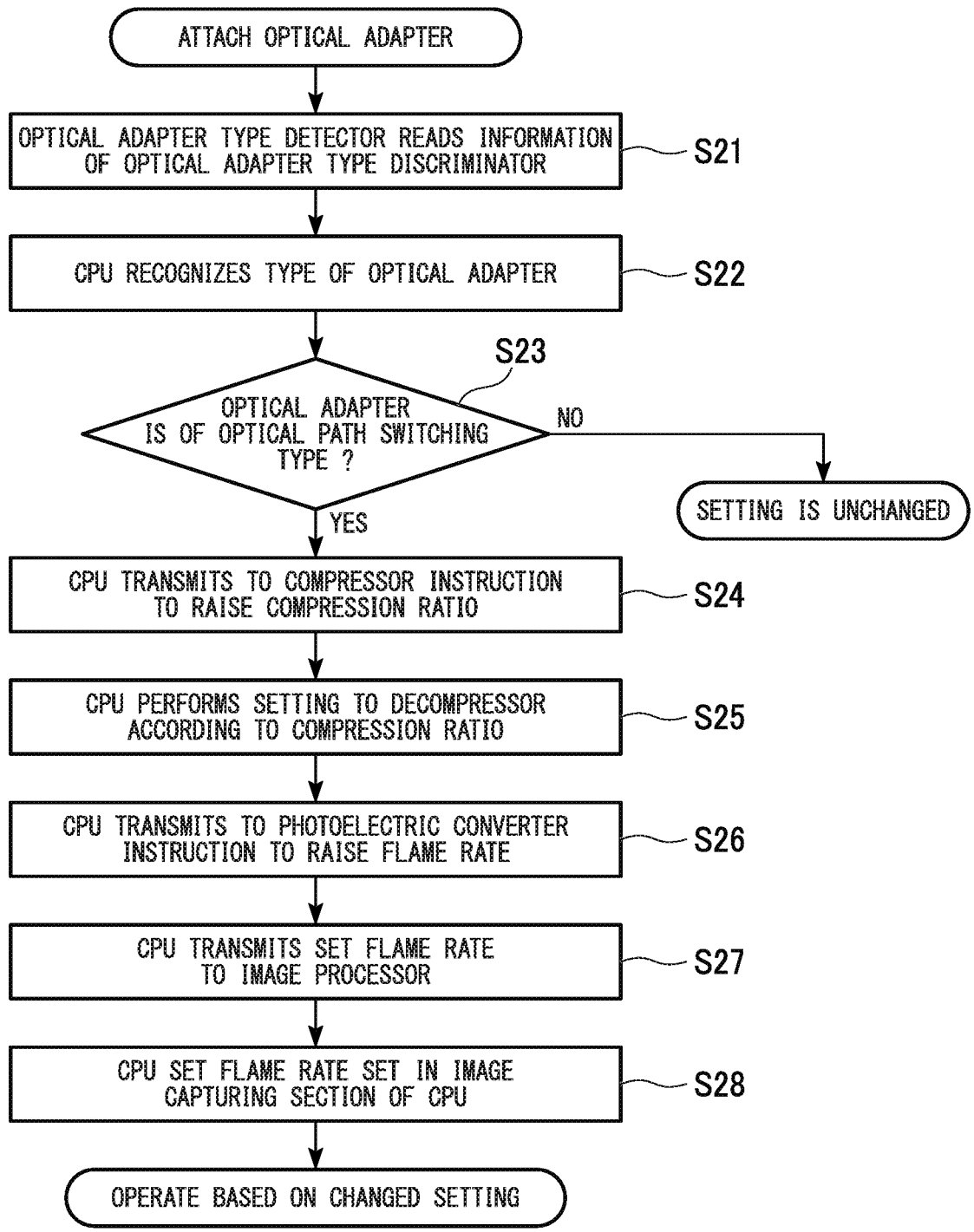
FIG. 4 is a flowchart showing a frame rate/compression ratio changing process based on the type of the optical adapter of the endoscope apparatus according to a second embodiment of the present invention.

Next, a frame rate/compression ratio changing process based on the type of the optical adapter of the endoscope apparatus according to the second embodiment of the present invention will be described. FIG. 4 is a flowchart showing a frame rate/compression ratio changing process based on the type of the optical adapter of the endoscope apparatus according to the present embodiment. In the present embodiment, when the type of the optical adapter 2 is optical path switching type, the frame rate of the photoelectric conversion in the photoelectric converter 31 is increased and the compression ratio in the compression of the video signal by the compressor 32 is increased.

When the apparatus is activated, first, the optical adapter type detector 55 of the main body section 5 reads the information (data) relating to the optical adapter type discriminator 21 of the optical adapter 2 (step S21) and transmits it to the CPU 57. The CPU 57 determines the type of the optical adapter type discriminator 21 based on the transmitted data (step S22). In the CPU 57, the type information relating to the type of the optical adapter is stored as a database, and by determining the type, it is recognized whether or not the optical adapter 2 is of optical path switching type (step S23).

When the optical adapter 2 is not of optical path switching type, setting of the compression ratio and the frame rate is not changed. When the optical adapter 2 is of optical path switching type, the CPU 57 determines the frame rate/compression ratio so as to achieve a transmission capable transmission rate.

FIG. 5 is a table showing the correspondence between the length of the insertion section 4, transmission capable transmission rate, and frame rate/compression ratio, in the frame rate/compression ratio changing process based on the type of the optical adapter of the endoscope apparatus according to the present embodiment. As shown in the table of FIG. 5, the transmission capable transmission rate and the frame rate/compression ratio are determined in advance for each length of the insertion section 4. Based on this table, the CPU 57 decides the frame rate/compression ratio so as to achieve a transmission capable transmission rate, and transmits an instruction to increase (set) the compression ratio to the compressor 32 via the control IF sections 54 and 34 (step S24).

Further, the CPU 57 sets the decompression ratio of the decompressor 52 so as to correspond to the compression ratio set by the compressor 32 (step S25). As a result, the compressor 32 compresses the video signal at the set compression ratio, and the decompressor 52 decompresses with the decompression ratio corresponding to the set compression ratio.

Further, the CPU 57 transmits an instruction to raise (set) the frame rate of the photoelectric conversion to the photoelectric converter 31 (step S26). As a result, the photoelectric converter 31 performs photoelectric conversion at the set frame rate to generate a video signal.

Further, the CPU 57 transmits the set frame rate to the image processor 53 (step S27). As a result, the image processor 53 performs image processing on the video signal based on the set frame rate.

Further, the CPU 57 sets the set frame rate in the image capturing section in the CPU 57 (step S28). As a result, the CPU 57 obtains image data from the image processor 57 based on the set frame rate, displays the image data on the display section 59, and records still image or moving image on the recording medium 58.

By performing the frame rate/compression ratio changing process in this way, it is possible to perform long-length transmission of image data. Further, since the frame rate and the compression ratio are determined by automatically determining the type of the optical adapter, complicated work is unnecessary.

In this embodiment, since the compression ratio changing process based on the type of the insertion section 4 is not performed, the insertion section type discriminator 41 and the insertion section type detector 56 in the configuration of FIG. 1 are not required.

Figure 6:
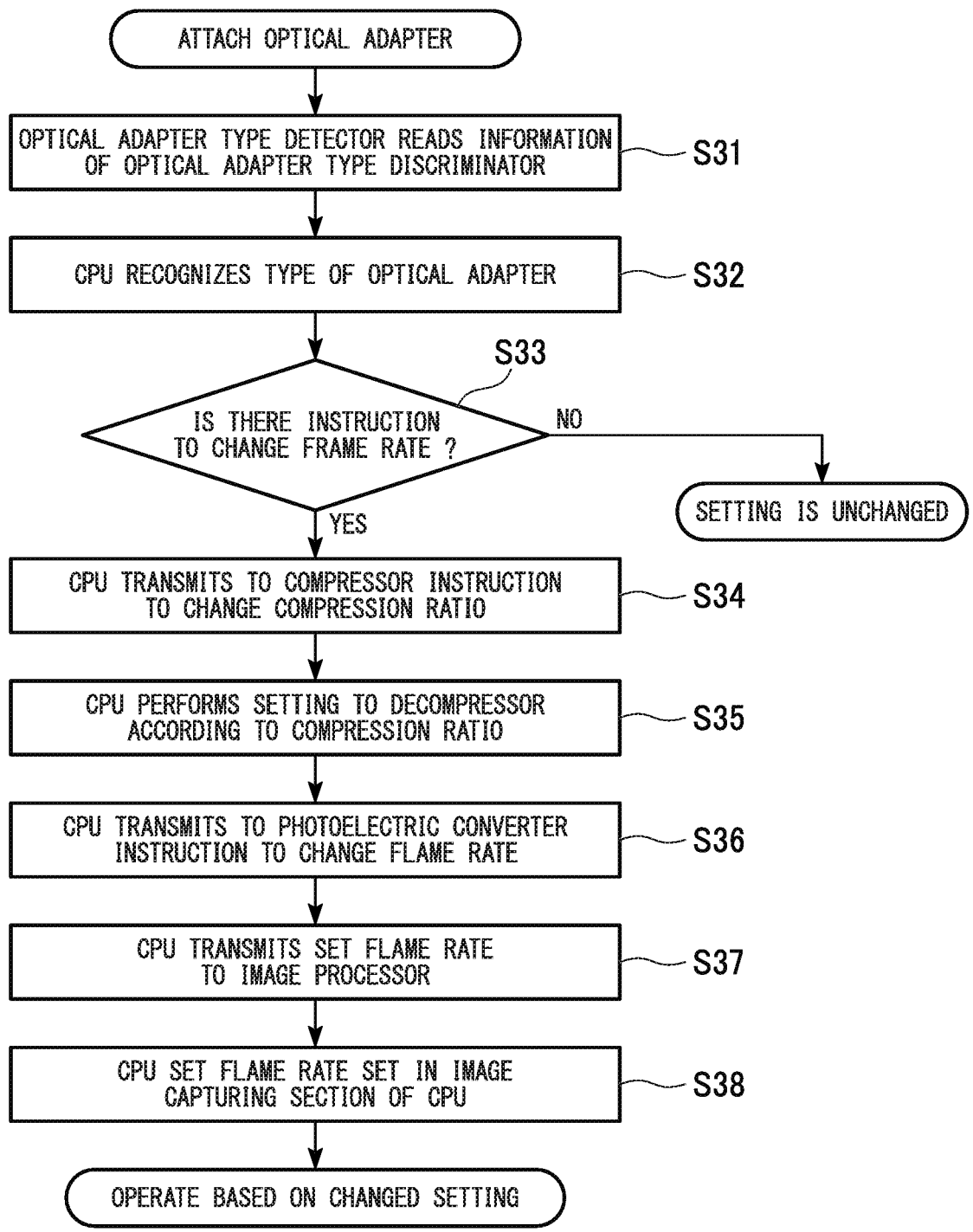
FIG. 6 is a flowchart showing a frame rate/compression ratio changing process based on the mode of the optical adapter of the endoscope apparatus according to a third embodiment of the present invention.

Next, the frame rate/compression ratio changing process based on the mode of the optical adapter of the endoscope apparatus according to the third embodiment of the present invention will be described. FIG. 6 is a flowchart showing a frame rate/compression ratio changing process based on the mode of the optical adapter of the endoscope apparatus according to the present embodiment. In this embodiment, the frame rate of the photoelectric conversion in the photoelectric converter 31 and the compression ratio in the compression of the video signal by the compressor 32 are changed according to the mode of the optical adapter 2.

When the apparatus is activated, first, the optical adapter type detector 55 of the main body section 5 reads the information (data) relating to the optical adapter type discriminator 21 of the optical adapter 2 (step S31) and transmits it to the CPU 57. The CPU 57 determines the type of the optical adapter type discriminator 21 based on the transmitted data (step S32). Here, in the present embodiment, the operation section 60 receives an instruction to change the frame rate, and the mode of the optical adapter is changed. That is, the CPU 57 determines whether or not there is an instruction to change the frame rate (instruction to change the setting of the frame rate) from the operation section 60 (step S33).

When there is no instruction to change the frame rate, the setting of the compression ratio and the frame rate is not changed. When there is an instruction to change the frame rate, the CPU 57 decides a compression ratio so as to achieve a transmission capable transmission rate, and transmits an instruction to change (set) the compression ratio to the compressor 32 via the control IF sections 54 and 34 (step S34).

Further, the CPU 57 sets the decompression ratio of the decompressor 52 so as to correspond to the compression ratio set in the compressor 32 (step S35). As a result, the compressor 32 compresses the video signal at the set compression ratio, and the decompressor 52 decompresses with the decompression ratio corresponding to the set compression ratio.

Further, the CPU 57 transmits an instruction to change (set) the frame rate of the photoelectric conversion to the photoelectric converter 31 (step S36). As a result, the photoelectric converter 31 performs photoelectric conversion at the set frame rate to generate a video signal.

Further, the CPU 57 transmits the set frame rate to the image processor 53 (step S37). As a result, the image processor 53 performs image processing on the video signal based on the set frame rate.

Further, the CPU 57 sets the set frame rate in the image capturing section in the CPU 57 (step S38). As a result, the CPU 57 obtains image data from the image processor 57 based on the set frame rate, displays the image data on the display section 59, and records still image or moving image on the recording medium 58.

By performing the frame rate/compression ratio changing process in this way, it is possible to perform long-length transmission of image data. Further, since the frame rate and the compression ratio are determined by automatically determining the type of the optical adapter and the type of the insertion section, complicated work is unnecessary.

In this embodiment, since the compression ratio changing process based on the type of the insertion section 4 is not performed, the insertion section type discriminator 41 and the insertion section type detector 56 in the configuration of FIG. 1 are not required.

In the above description, the compression ratio changing process is performed based on the length of the insertion section in the first embodiment, the frame rate/compression ratio changing process based on the type of the optical adapter is performed in the second embodiment, and the frame rate/compression ratio changing process based on the mode of the optical adapter is performed in the third embodiment. These embodiments may be combined as appropriate. That is, the frame rate/compression ratio changing process may be performed based on two or more of the type/mode of the optical adapter and the length of the insertion section.

In the above description, the compression ratio is set based on the length of the insertion section as the type of the insertion section. The compression ratio may be set based on the size of the diameter of the transmission path in the insertion section or the like as the type of the insertion section.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An endoscope apparatus comprising:
   an imager having a photoelectric converter that performs a photoelectric conversion of an optical signal into a video signal, and a compressor that compresses the video signal; and
   a controller configured to:
      determine a type of an insertion section; and
      change a compression ratio in a compression of the video signal in accordance with the determined type of the insertion section.

2. The endoscope apparatus according to claim 1, wherein the controller is further configured to change a frame rate of the photoelectric conversion in accordance with a preset condition.

3. The endoscope apparatus according to claim 1, wherein the type of the insertion section includes information on a length of the insertion section,
   the controller is configured to increase the compression ratio as the length of the insertion section is longer.

4. The endoscope apparatus according to claim 1, wherein the type of the insertion section includes information on a size of a diameter of a transmission line included in the insertion section, and
   the controller is configured to change the compression ratio in accordance with the size of the diameter of the transmission line included in the insertion section.

5. An endoscope apparatus comprising:
   an imager having a photoelectric converter that performs a photoelectric conversion of an optical signal into a video signal, and a compressor that compresses the video signal; and
   a controller configured to:
      determine a type of an optical adapter mounted on the imager; and
      change at least one of a compression ratio and a frame rate of the photoelectric conversion in accordance with the determined type of the optical adapter.

6. The endoscope apparatus according to claim 5, wherein, when the type of the optical adapter is a type capable of switching a plurality of optical paths, the controller is configured to increase the compression ratio.

7. The endoscope apparatus according to claim 5, wherein, when the type of the optical adapter is a type capable of switching a plurality of optical paths, the controller is configured to increase the frame rate.

8. The endoscope apparatus according to claim 5, wherein, when there is an instruction by an operation section to change the frame rate in accordance with the type of the optical adapter, the controller is configured to change the frame rate.

9. An imaging method using an endoscope apparatus including an imager having a photoelectric converter that performs a photoelectric conversion of an optical signal into a video signal and a compressor that compresses the video signal, wherein the imaging method includes:
   determining a type of an insertion section; and
   changing a compression ratio of the compressor in accordance with the determined type of the insertion section.

10. An imaging method using an endoscope apparatus including an imager having a photoelectric converter that performs a photoelectric conversion of an optical signal into a video signal and a compressor that compresses the video signal, wherein the imaging method includes:
   determining a type of an optical adapter mounted on the imager; and
   changing a compression ratio of the compressor and a frame rate of the photoelectric conversion in accordance with the determined type of the optical adapter.

* * * * *